US009765298B2

(12) United States Patent
Terzic et al.

(10) Patent No.: US 9,765,298 B2
(45) Date of Patent: *Sep. 19, 2017

(54) METHODS AND MATERIALS FOR PROVIDING CARDIAC CELLS

(75) Inventors: Andre Terzic, Rochester, MN (US); Atta Behfar, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 1727 days.

This patent is subject to a terminal disclaimer.

(21) Appl. No.: 11/674,461

(22) Filed: Feb. 13, 2007

(65) Prior Publication Data

US 2008/0019944 A1    Jan. 24, 2008

Related U.S. Application Data

(60) Provisional application No. 60/832,845, filed on Jul. 24, 2006.

(51) Int. Cl.
*C12N 5/077* (2010.01)

(52) U.S. Cl.
CPC ...... *C12N 5/0657* (2013.01); *C12N 2501/105* (2013.01); *C12N 2501/119* (2013.01); *C12N 2501/15* (2013.01); *C12N 2501/155* (2013.01); *C12N 2501/165* (2013.01); *C12N 2501/235* (2013.01); *C12N 2501/2306* (2013.01); *C12N 2501/25* (2013.01); *C12N 2501/385* (2013.01); *C12N 2501/70* (2013.01); *C12N 2506/21* (2013.01)

(58) Field of Classification Search
None
See application file for complete search history.

(56) References Cited

U.S. PATENT DOCUMENTS

| | | | |
|---|---|---|---|
| 5,839,438 A | 11/1998 | Graettinger et al. |
| 6,833,269 B2 | 12/2004 | Carpenter |
| 7,425,448 B2 | 9/2008 | Xu |
| 7,452,718 B2 | 11/2008 | Gold et al. |

(Continued)

FOREIGN PATENT DOCUMENTS

| | | |
|---|---|---|
| JP | 2002-511094 | 4/2002 |
| JP | 2007-517831 | 7/2007 |

(Continued)

OTHER PUBLICATIONS

Zhao P et al. 2005. Human amniotic mesenchymal cells have some characteristics of cardiomyocytes. Transplantation 79: 528-535.*

(Continued)

*Primary Examiner* — Sharmila G. Landau
*Assistant Examiner* — Stephanie McNeil
(74) *Attorney, Agent, or Firm* — Fish & Richardson P.C.

(57) ABSTRACT

This document provides methods and materials relating to cardiac cells. For example, this document provides methods and materials that can be used to obtain cells having the ability to differentiate into cardiomyocytes. Such cells can be used to repair damaged heart tissue. For example, cells having the ability to differentiate into cardiomyocytes can be used to repair or regenerate heart tissue in patients with a cardiac condition (e.g., ischemic cardiomyopathy, myocardial infarction, or heart failure).

17 Claims, 3 Drawing Sheets

(56) References Cited

U.S. PATENT DOCUMENTS

| | | |
|---|---|---|
| 7,732,199 B2 | 6/2010 | Xu et al. |
| 8,071,380 B2 | 12/2011 | Cossu et al. |
| 8,158,421 B2 | 4/2012 | Passier et al. |
| 8,173,118 B2 | 5/2012 | Terzic et al. |
| 2002/0039557 A1 | 4/2002 | White |
| 2002/0061837 A1 | 5/2002 | Lough et al. |
| 2003/0224345 A1 | 12/2003 | West et al. |
| 2003/0229908 A1 | 12/2003 | Cibelli et al. |
| 2005/0054092 A1 | 3/2005 | Xu et al. |
| 2005/0164382 A1 | 7/2005 | Xu |
| 2007/0274970 A1 | 11/2007 | Gordon et al. |
| 2008/0019944 A1 | 1/2008 | Terzic et al. |
| 2008/0057028 A1 | 3/2008 | Alitalo et al. |
| 2009/0098563 A1 | 4/2009 | Penning |
| 2010/0009399 A1 | 1/2010 | Sartipy et al. |
| 2010/0166714 A1 | 7/2010 | Chien et al. |
| 2010/0189697 A1 | 7/2010 | Terzic et al. |
| 2011/0117065 A1 | 5/2011 | Terzic et al. |
| 2012/0100533 A1 | 4/2012 | Terzic et al. |
| 2012/0178164 A1 | 7/2012 | Terzic et al. |
| 2014/0348803 A1 | 11/2014 | Terzic et al. |

FOREIGN PATENT DOCUMENTS

| | | |
|---|---|---|
| JP | 2007-537692 | 12/2007 |
| WO | 2005/038454 | 4/2005 |
| WO | 2005/090558 | 9/2005 |
| WO | 2006/015127 | 2/2006 |
| WO | WO 2006/032054 | 3/2006 |
| WO | WO 2006/081190 | 8/2006 |
| WO | WO 2007/012009 | 1/2007 |
| WO | WO 2008/034430 | 3/2008 |
| WO | WO 2008/109839 | 9/2008 |
| WO | WO 2009/145761 | 12/2009 |
| WO | WO 2009/151907 | 12/2009 |
| WO | WO 2010/133686 | 11/2010 |
| WO | WO 2010/135555 | 11/2010 |

OTHER PUBLICATIONS

Wojakowski W et al. 2004. Mobilization of CD34/CXCR4+, CD34/CD117+, c-met+ stem cells and mononuclear cells expressing early cardiac, muscle, and endothelial markers into peripheral blood in patients with acute myocardial infarction. Circ 110: 3213-3220.*

Itescu S et al. 2003. New directions in strategies using cell therapy for heart disease. J Mol Med 81: 288-296.*

Behfar et al., "Newly Identified Cardiopoietic Stem Cell Population Recruited by TNF-α from Pluripotent Embryonic Cells," *Circulation*, 2004, 110(17):III-302, Abstract No. 1444.

Behfar et al., "Cardiopoietic programming of embryonic stem cells for tumor-free heart repair," *J. Exp. Med.*, 2007, 204(2):405-420.

Méry et al., "Commitment of embryonic stem cells toward a cardiac lineage: molecular mechanisms and evidence for a promising therapeutic approach for heart failure," *J. Muscle Res. Cell Motility*, 2003, 24:269-274.

Mummery et al., "Differentiation of Human Embryonic Stem Cells to Cardiomyocytes. Role of Coculture With Visceral Endoderm-Like Cells," *Circulation*, 2002, 107:2733-2740.

Rudy-Reil and Lough, "Avian Precardiac Endoderm-Mesoderm Induces Cardiac Myocyte Differentiation in Murine Embryonic Stem Cells," *Circ. Res.*, 2004, 94:e107-e116.

Anversa and Nadal-Ginard, "Myocyte renewal and ventricular remodelling," *Nature*, 2002, 415:240-243.

Behfar and Terzic, "Derivation of a cardiopoietic population from human mesenchymal stem cells yields cardiac progeny," *Nat. Clin. Pract. Cardiovasc. Med.*, 2006, 3(Suppl 1):S78-S82.

Behfar et al., "Stem cell differentiation requires a paracrine pathway in the heart," *FASEB J.*, 2002, 16:1558-1566.

Behfar et al., Administration of Allogenic Stem Cells Dosed to Secure Cardiogenesis and Sustained Infarct Repair, *Ann. N.Y. Acad. Sci.*, 2005, 1049:189-198.

Beltrami et al., "Adult Cardiac Stem Cells Are Multipotent and Support Myocardial Regeneration," *Cell*, 2003, 114:763-776.

Caplice et al., "Cell therapy for cardiovascular disease: what cells, what diseases and for whom?" *Nat. Clin. Pract. Cardiovasc. Med.*, 2005, 2:37-43.

Dawn and Bolli, "Bone marrow cells for cardiac regeneration: the quest for the protagonist continues," *Cardiovasc. Res.*, 2005, 65(2):293-295.

Dimmeler et al., "Unchain my heart: the scientific foundations of cardiac repair," *J. Clin. Invest.*, 2005, 115(3):572-583.

Fernández-Avilés et al., "Experimental and Clinical Regenerative Capability of Human Bone Marrow Cells After Myocardial Infarction," *Circ. Res.*, 2004, 95:742-748.

Fijnvandraat et al., "Cardiomyocytes purified from differentiated embryonic stem cells exhibit characteristics of early chamber myocardium," *J. Mol. Cell. Cardiol.*, 2003, 35(12):1461-1472.

Foley and Mercola, "Heart Induction: Embryology to Cardiomyocyte Regeneration," *Trends Cardiovasc. Med.*, 2004, 14:121-125.

Fraidenraich et al., "Rescue of Cardiac Defects in id Knockout Embryos by Injection of Embryonic Stem Cells," *Science*, 2004, 306:247-252.

Fukuda, "Molecular characterization of regenerated cardiomyocytes derived from adult mesenchymal stem cells," *Congenital Anomalies*, 2002, 42:1-9.

Fukuda, "Development of Regenerative Cardiomyocytes from Mesenchymal Stem Cells for Cardiovascular Tissue Engineering," *Artificial Organs*, 2001, 25(3):187-193.

Gnecchi et al., "Paracrine action accounts for marked protection of ischemic heart by Akt-modified mesenchymal stem cells," *Nat. Med.*, 2005, 11(4):367-368.

Hodgson et al., "Cellular remodeling in heart failure disrupts $K_{ATP}$ channel-dependent stress tolerance," *EMBO J.*, 2003, 22(8):1732-1742.

Hodgson et al., "Stable benefit of embryonic stem cell therapy in myocardial infarction," *Am. J. Physiol. Heart Circ. Physiol.*, 2004, 287:H471-H479.

Jiang et al., "Pluripotency of mesenchymal stem cells derived from adult marrow," *Nature*, 2002, 418:41-49.

Koh et al., "Co-culture of human CD34+ cells with mesenchymal stem cells increases the survival of CD34+ cells against the 5-aza-deoxycytidine- or trichostatin A-induced cell death," *Biochem. Biophys. Res. Commun.*, 2005, 329:1039-1045.

Kucia et al., "Cells Expressing Early Cardiac Markers Reside in the Bone Marrow and Are Mobilized Into the Peripheral Blood After Myocardial Infarction," *Circ. Res.*, 2004, 95:1191-1199.

Laugwitz et al., "Postnatal isl1+ cardioblasts enter fully differentiated cardiomyocyte lineages," *Nature*, 2005, 433:647-653.

Menasche et al., "Autologous Skeletal Myoblast Transplantation for Severe Postinfarction Left Ventricular Dysfunction," *J. Am. Coll. Cardiol.*, 2003, 41(7):1078-1083.

Menasché, "Embryonic stem cells pace the heart," *Nat. Biotechnol.*, 2004, 22(10):1237-1238.

Murry et al., "Hematopoietic stem cells do not transdifferentiate into cardiac myocytes in myocardial infarcts," *Nature*, 2004, 428:664-668.

Nygren et al., "Bone marrow-derived hematopoietic cells generate cardiomyocytes at a low frequency through cell fusion, but not transdifferentiation," *Nat. Med.*, 2004, 10(5):494-501.

Olson and Schneider, "Sizing up the heart: Development redux in disease," *Genes Dev.*, 2003, 17:1937-1956.

Orlic et al., "Bone marrow cells regenerate infarcted myocardium," *Nature*, 2001, 410:701-705.

Perez-Terzic et al., "Structural Adaptation of the Nuclear Pore Complex in Stem Cell-Derived Cardiomyocytes," *Circ. Res.*, 2003, 92:444-452.

Perin et al., "Improved Exercise Capacity and Ischemia 6 and 12 Months After Transendocardial Injection of Autologous Bone Marrow Mononuclear Cells for Ischemic Cardiomyopathy," *Circulation*, 2004, 110(suppl II):II-213-II-218.

Pittenger and Martin, "Mesenchymal Stem Cells and Their Potential as Cardiac Therapeutics," *Circ. Res.*, 2004, 95:9-20.

(56) References Cited

OTHER PUBLICATIONS

Rangappa et al., "Cardiomyocyte-mediated contact programs human mesenchymal stem cells to express cardiogenic phenotype," *J. Thorac. Cardiovasc. Surg.*, 2003, 126:124-132.

Schächinger et al., "Transplantation of Progenitor Cells and Regeneration Enhancement in Acute Myocardial Infarction. Final One-Year Results of the TOPCARE-AMI Trial," *J. Am. Coll. Cardiol.*, 2004, 44(8):1690-1699.

Shim et al., "Ex vivo differentiation of human adult bone marrow stem cells into cardiomyocyte-like cells," *Biochem. Biophys. Res. Commun.*, 2004, 324:481-488.

Takeda et al., "Can the life span of human marrow stromal cells be prolonged by bmi-1, E6, E7, and/or telomerase without affecting cardiomyogenic differentiation?" *J. Gene Med.*, 2004, 6(8):833-845.

Toma et al., "Human Mesenchymal stem Cells Differentiate to a Cardiomyocyte Phenotype in the Adult Murine Heart," *Circulation*, 2002, 105:93-98.

Tomita et al., "Autologous Transplantation of Bone Marrow Cells Improves Damaged Heart Function," *Circulation*, 1999, 100(suppl. II):II-247-II-256.

Towbin and Bowles, "The failing heart," *Nature*, 2002, 415:227-233.

Wollert and Drexler, "Mesenchymal stem cells for myocardial infarction: Promises and Pitfalls," *Circ. Res.*, 2005, 96:151-163.

Wollert et al., "Intracoronary autologous bone-marrow cell transfer after myocardial infarction: the BOOST randomised controlled clinical trial," *Lancet*, 2004, 364:141-148.

Wollert and Drexler, "Clinical Applications of Stem Cells for the Heart," *Circ. Res.*, 2005, 96:151-163.

Xaymardan et al., Platelet-Derived Growth Factor-AB Promotes the Generation of Adult Bone Marrow-Derived Cardiac Myocytes, *Circ. Res.*, 2004, 94:e39-e45.

Xu et al., "Mesenchymal Stem Cells from Adult Human Bone Marrow Differentiate into a Cardiomyocyte Phenotype In Vitro," *Exp. Biol. Med.*, 2004, 229:623-631.

Yoon et al., "Myocardial regeneration with bone-marrow-derived stem cells," *Biol. Cell*, 2005, 97:253-263.

Meyer et al., "A fluorescent reporter gene as a marker for ventricular specification in ES-derived cardiac cells," *FEBS Lett.*, 2000, 478:151-158.

Dawn, B., et al., "Cardiac stem cells delivered intravascularly traverse the vessel barrier, regenerate infracted myocardium, and improve cardiac function," PNAS, vol. 102(10):3766-3771 (2005).

Baddoo, et al., Characterization of Mesenchymal Stem Cells Isolated from Murine Bone Marrow by Negative Selection,? *Journal of Cellular Biochemistry*, 89?1235-1249 (2003).

Solloway, et al., "Molecular pathways myocardial development: a stem cell perspective," *Cardiovascular Research*, 58 (2003) 264-277.

Boheler, et al, "Differentiation of Pluripotent Embryonic Stem Cells Into Cardiomyocytes," *Circulation Research*, Aug. 9, 2002.

Aicher et al., "Essential role of endothelial nitric oxide synthase for mobilization of stem and progenitor cells," *Nature Medicine*, 2003, 9: 1370-1376.

Andree et al., "BMP-2 induces ectopic expression of cardiac lineage markers and interferes with somite formation in chicken embryos," *Mech. Dev.*, 1998, 70(1-2):119-131.

Arrell et al., "Proteomic analysis of pharmacologically perconditioned cardiomyocytes reveals novel phosphorylation of myosin light chain 1," *Circulation Research*, 2001, 89: 480-487.

Askari et al., "Effect of stromal-cell-derived factor 1 on stem-cell homing and tissue regeneration in ischaemic cardiomyopathy," *Mechanisms of Disease*, 2003, 362: 697-703.

Beltrami et al., "Evidence that human cardiac myocytes divide after myocardial infarction," *N. Engl. J. Med.*, 2001, 344:1750-1757.

Bondue et al., "Mesp1 acts as a master regulator of multipotent cardiovascular progenitor specification," *Cell Stem Cell*, 2008, 3(1): 69-84.

Britten et al., "Infarct remodeling after intracoronary progenitor cell treatment in patients with acute myocardial infarction (TOPCARE-AMI): Mechanistic insights from serial contrast-enhanced magnetic resonance imaging," *Circulation*, 2003, pp. 2212-2218.

Chien et al., ES Cells to the Rescue, *Science*, 2004, 306:239-240.

Daniels et al., "Imatinib mesylate inhibits the profibrogenic activity of TGF-β and prevents bleomycin mediated lung fibrosis," *J Clin invest*, 2004, 114: 1308-1316.

Drukker et al., "Characterization of the expression of MHC proteins in human embryonic stem cells," *PNAS*, 2002, 99(15): 9864-9869.

Edgeworth et al., "Ionomycin-regulated phosphorylation of the myeloid calcium-binding protein p14," *Nature*, 1989, 342:189-192.

Erdo et al., "Host-dependent tumorigenesis of embryonic stem cell transplanation in experimental stroke," *J. Cereb. Blood Flow Metab.*, 2003, 23:780-785.

Frandrich et al., "Preimplantation-stage stem cells induce long-term allogeneic graft acceptance without supplementary host conditioning," *Nature Medicine*, 2002, 8(2): 171-178.

Gepstein, "Derivation and potential applications of human embryonic stem cells," *Circ. Res.*, 2002, 91:866-876.

Gharandaghi et al., "Mass spectrometric identification of proteins from silver-stained polyacrylamide gel: A method for the removal of silver ions to enhance sensitiviry," *Electrophoresis*, 1999, 20: 601-605.

Ghosh et al., "Physical interaction between TBX5 and MEF2C is required for early heart development," *Molecular and Cellular Biology*, 2009, 29(8): 2205-2218.

He et al., "Human embryonic stem cells develop into multiple types of cardiac myocytes: Action potential characterization," *Circ. Res.*, 2003, 93:32-39.

Jiang et al., "Common Role for Each of the cGATA-4/5/6 Genes in the Regulation of Cardiac Morphogenesis," *Dev. Genet.*, 1998, 22:263-277.

Kane et al., "ATP-Sensitive K+ challel knockout compromises the metabolic benefit of exercise training, resulting in cardiac deficits," *Diabetes*, 2004, 53: 169-175.

Levenberg et al., "Endothelial cells derived from human embryonic stem cells," *PNAS*, 2002, 99: 4391-4396.

Lila et al., "Human leukocyte antigen-G expression after heart transplantation is assocaited with a reduced indicence of rejection," *Circulation*, 2002, 105: 1949-1954.

Lin et al., "Control of mouse cardiac morphogenesis and myogenesis by tanscription factor MEF2C," *Science* 1997, 276: 1404-1407.

Locksley et al., "The TNG and TNF receptor superfamilies: Integrating mammalian biology," *Cell*, 2001, 104: 487-501.

Lutz et al., "Nucleoside diphosphate kinase-mediated activation of heterotrimeric G proteins," *Meth. Enzymol.*, 2004, 390:403-418.

Maltsev et al., "Cardiomyocytes differentiated in vitro from embryonic stem cells developmentally express cardiac-specific genes and ionic currents," *Circulation Research*, 1994, 75: 233-244.

Mangi et al., "Mesenchymal stem cells modified with Akt prevent remodeling and restore performance of infarcted hearts," *Nature Medicine*, 2003, 9: 1195-1201.

Min et al., "Long-term improvement of cardiac function in rats after infarction by transplantation of embryonic stem cells," *J. Thoracic Cardiovasc. Surg.*, 2003, 125:361-369.

Min et al., "Transplantation of embryonic stem cells improves cardiac function in postinfarcted rats," *J. Appl. Physiol.*, 2002, 92:288-296.

Mohri et al., "Expression of cofilin isoforms during development of mouse striated muscles," *J. Muscle Res. Cell. Motil.*, 2000, 21:49-57.

Murry et al., "Cellular therapies for myocardial infarct repair," *Cold Spring Harbor Symp. Quant. Biol.*, 2002, 67:519-526.

Nakano et al., "Tumor necrosis factor-alpha confers resistance to hypoxia injury in the adult mammalian cardiac myocytes," *Circulation*, 1998, 97: 1392-1400.

Nir et al., "Human embryonic stem cells for cardiovascular repair," *Cardiovasc. Res.*, 2003, 58:313-323.

Obinata et al., "Low molecular-weight G-actin binding proteins involved in the regulation of actin assembly during myofibrillogenesis," *Cell Struct. Funct.*, 1997, 22:181-189.

(56) References Cited

OTHER PUBLICATIONS

O'Cochlain et al., "Transgenic overexpression of human DMPK accumulates into hypertrophic cardiomyopathy, myotonic myopathy and hypotension traits of myotonic dystrophy," Human Molecular Genetics, 2004, 13(20): 2505-2518.
Oh et al., "Cardiac progenitor cells from adult myocardium: Homing, differentiation, and fusion after infarction," Proc. Natl. Acad. Sci. USA, 2003, 100:12313-12318.
Orlic et al., "Stem cells for myocardial regeneration," Circ. Res., 2002, 91:1092-1102.
Perez-Terzic et al., "Directed inhibition of nuclear import in cellular hypertrophy," J. Biological Chemistry, 2001, 276(23): 20566-20571.
Rajasingh et al., "STAT3-dependent mouse embryonic stem cell differentiation into cardiomyocytes analysis of molecular signaling and therapeutic efficacy of cardiomyocyte precommitted mES transplantation in a mouse model of myocardial infarction," Circulation Research, 2007, 101(9): 910-918.
Sachinidis et al., "Cardiac specific differentiation of mouse embryonic stem cells," Cardiovasc Res., 2003, 58:278-291.
Sadygov et al., "Large-scale database searching using tandem mass spectra: Looking up the answer in the back of the book," Nature, 2004, 1(3): 195-202.
Sauer et al., "Involvement of reactive oxygen species in cardiotrophin-1-induced roliferation of cardiomyocytes differentiated from murine embryonic stem cells," Exp. Cell. Res., 2004, 294: 313-324.
Seino and Mike, "Physiological and pathophysiological roles of ATP-sensitive K+ Channels," Biophysics & Molecular Biology, 2003, 81: 133-176.
Shachauf et al., "MYC inactivation uncovers pluripotent differentiation and tumour dormancy in hepatocellular cancer," Nature, 2004, 431: 1112-1117.
Shevchenko et al., "Mass spectrometric sequencing of proteins from silver-stained polyacrylamide gels," Anal. Chem, 1996, 68: 850-858.
Sivasubramanian et al., "Left ventricular remodeling in transgenic mice with cardiac restricted overexpression of tumor necrosis factor," Circulation, 2001, 104: 826-831.
Smart et al., "A differential screen for putative targets of the bHLH transcription facto Handl in cardian morphogenesis," Gene Expr. Patterns, 2002, 2:61-67.
Srivasta et al., "A genetic blueprint for cardiac development," Nature, 2000, 407: 221-226.
Terzic et al., "Structural adaptation of the nuclear pore complex in stem cell-derived cardiomyocytes," 2003, Circ. Res., 92:444-452.
Thompson et al., "Comparison of intracardiac cell transplantation: autologous skeletal myoblasts versus bone marrow cells," Circulation, 2003, 108:II264-II271.
Thomson et al., "Embryonic stem cell lines derived from human blastocysts," Science, 1998, 282: 1145-1147.
Vassilopoulos et al., "Transplanted bone marrow regenerates liver by cell fusion," Nature, 2003, 422: 901-904.
Wang et al., "Cell fusion is the principal source of bone-marrow-derived hepatocytes," Nature, 2003, 422: 897-901.
Wu et al., "Small molecules that induce cardiomyogenesis in embryonic stem cells," J. Am. Chem. Soc., 2004, 126(6): 1590-1591.
Xin et al., "Oestrogen protects FKBP12.6 null mice from cardiac hypertrophy," Nature, 2002, 416:334-338.
Yang et al., "VEGF enhances functional improvement of postinfarcted hearts by transplantation of ESC-differentiated cells," J. Appl. Physiol., 2002, 93: 1140-1151.
Zingman et al., Tandem function of nucleotide binding domains confers competence to sultonylurea receptor in gating ATP-sensitive K+ channels, J. Biol. Chem., 2002, 277(16): 14206-14210.
Tsuji, H., et al., "Xenografted Human Amniotic Membrane-Derived Mesenchymal Stem Cells Are Immunologically Tolerated and Transdifferentiated Into Cardiomyocytes," Circulation Research, 106:1613-1623 (2010).
Tsuji, H., et al., "Amniotic Membrane-Derived Stem Cell, Supplemental materials, Figure Legends for Supplemental Material," 205260-R3, pp. 1-26 (2009).
"AMS 5 Correlation" http://www.math.ntua.ge-fouskakis/SS/correlation.pdf (Jul. 7, 2013).
Abbott et al., "Stromal Cell-Derived Factor-1 Plays a Critical Role in Stem Cell Recruitment to the Heart After Myocardial Infarction but Is Not Sufficient to Induce Homing in the Absence of Injury," Circulation, 2004, 110:3300-3305.
Abdel-Latif et al., "Adult bone marrow-derived cells for cardiac repair: a systematic review and meta-analysis," Arch intern Med., 2007, 167:989-997.
Alviano et al., "Term amniotic membrane is a high throughput source for multipotent mesenchymal stem cells with the ability to differentiate into endothelial cells in vitro," BioMed Central Developmental Biology, Feb. 2007, 7:11, 14 pages.
Assmus et al., "Transcoronary transplantation of progenitor cells after myocardial infarction," N. Engl. J. Med., 2006, 355:1222-1232.
Ayach et al. "CXCR4 improves cardiac remodeling and neovascularization and regulated inflammatory and progenitor stem cell mobilization post-myocardial infarction," J. Cardial Failure, 2006, 12(6):S43 (Abstract only).
Baba et al. "Flk1 + cardiac stem/progenitor cells derived from embryonic stem cells improve cardiac function in a dilated cardiomyopathy mouse model," Cardiovasc. Res., 2007, 76(1):119-131.
Baldwin et al., "Myogenic cytodifferentiation of the precardiac mesoderm in the rat," Differentiation, 1991, 47:163-172.
Barabasi and Oltvai, "Network biology: understanding the cell's functional organization," Nat. Rev. Genet., 2004, 5:101-113.
Bartunek et al. "Pretreatment of adult bone marrow mesenchymal stem cells with cardiomyogenic growth factors and repair of the chronically infarcted myocardium," Am. J. Phys: Heart and Circ. Phys., 2007 292 (2):H1095-H1104.
Behfar et al. "Guided Cardiopoiesis Enhances Therapeutic Benefit of Bone Marrow Human Mesenchymal Stem Cells in Chronic Myocardial Infarction," J. Amer. College of Cardiology, 2010, 56(9): 721-734.
Behfar et al., "Administration of allogenic stem cells dosed to secure cardiogenesis and sustained infarct repair," Ann. NY Acad. Sci., 2005, 1049:189-198.
Behfar et al., "Guided stem cell cardiopoietic: Discovery and translation," J Mol and Cell Cardioogy, 2008, 45:523-529.
Beqqali et al., "Genome-wide transcriptional profiling of human embryonic stem cells differentiating to cardiomyocytes," Stem Cells, 2006, 24:1956-1967.
Brewer et al., "GATA factors lie upstream of Nkx 2.5 in the transcriptional regulatory cascade that effects cardiogenesis," Stem Cells Dev., 2005, 14:425-439.
Buckingham et al., "Building the mammalian heart from two sources of myocardial cells," Nat. Rev. Genet., 2005, 6:826-835.
Ceradini and Gurtner, "Homing to hypoxia: HIF-1 as a mediator of progenitor cell recruitment to injured tissue," Trends Cardiovasc. Med., 2005, 15:57-63.
Ceradini et al., "Progenitor cell trafficking is regulated by hypoxic gradients through HIF-1induction of SDF-1," Nat. Med., 2004, 10:858-864.
Chen et al., "Myocardin: a component of a molecular switch for smooth muscle differentiation," J. Mol. Cell Cardiol., 2002, 34:1345-1356.
Chinese Office Action in Chinese Application No. 200980118954, dated Aug. 31, 2012, 17 pages.
Chung et al., "Mitochondrial oxidative metabolism is required for the cardiac differentiation of stem cells," Nat. Clin. Pract. Cardiovasc. Med., Feb. 2007, 4Suppl(1):S60-67.
Compernolle et al., "Cardia bifida, defective heart development and abnormal neural crest migration in embryos lacking hypoxia-inducible factor-1α," Cardiovasc. Res., 2003, 60:569-579.
Diaz and Gulino, "WHIM syndrome: a defect in CXCR4 signaling," Curr. Allergy Asthma Rep., 2005, 5:350-355.

(56) References Cited

OTHER PUBLICATIONS

Eisenberg and Eisenberg, "An in vitro analysis of myocardial potential indicates that phenotypic plasticity is an innate property of early embryonic tissue," *Stem Cells Dev.*, 2004, 13:614-624.
Ema et al., "Deletion of the selection cassette, but not cis-acting elements, in targeted Flk1-lacZ allele reveals Flk1 expression in multipotent mesodermal progenitors," Blood, 2006, 107:111-117.
European Office Action in European Application No. 05777528.0, dated Feb. 2, 1010, 6 pages.
European Office Action in European Application No. 05777528.0, dated Nov. 26, 2010, 5 pages.
European Office Action in European Application No. 10179541.7, dated Jun. 5, 2012, 5 pages.
Extended European Search Report in European Application No. 08731697.2, dated Mar. 10, 2011, 8 pages.
Extended European Search Report in European Application No. 09763198.0, dated Jun. 13, 2012, 11 pages.
Extended European Search Report in European Application No. 10179541.7, dated Nov. 24, 2010, 9 pages.
Faustino et al., "Genomic chart guiding embryonic stem cell cardiopolesis," *Genome Biol.*, 2008, 9(1):R6.
Feigner et al., "Enhanced gene delivery and mechanism studies with a novel series of cationic lipid formulations," *J. Biol. Chem.*, 1994, 269:2550-2561.
Gorlin et al., "WHIM syndrome, an autosomal dominant disorder: clinical, hematological, and molecular studies," *Am. J. Med. Genet.*, 2000, 91:368-376.
Hartmann et al., "The role of adhesion molecules and chemokine receptor CXCR4 (CD 184) in small cell lung cancer," *J. Biol. Regul. Homeost. Agents.*, 2004, 18:126-130.
Hass et al., "Different populations and sources of human mesenchymal stem cells (MSC): A comparison of adult and neo-natal tissue-derived MSC," Cell Communication and Signaling, 2011, 9:12, 14 pages.
Hernandez et al., "Mutations in the chemokine receptor gene CXCR4 are associated with WHIM syndrome, a combined immunodeficiency disease," Nat. Genet., 2003, 34:70-74.
Huber et al., "Haemangioblast commitment is initiated in the primitive streak of the mouse embryo," *Nature*, 2004, 432:625-630.
International Preliminary Report on Patentability in International Application No. PCT/US2008/064895, mailed Dec. 9, 2010, 7 pages.
International Preliminary Report on Patentability in International Application No. PCT/US2010/035616, dated Jul. 5, 2011, 10 pages.
International Preliminary Report on Patentability in International Application No. PCT/US2005/026800, mailed Apr. 26, 2007, 6 pages.
International Preliminary Report on Patentability in International Application No. PCT/US2009/044714, mailed Dec. 9, 2010, 9 pages.
International Preliminary Report Written on Patentability in PCT/US2008/056248, issued Sep. 8, 2009, 6 pages.
International Search Report and Written Opinion in Internatioanl Application No. PCT/US2008/064895, mailed Feb. 24, 2009, 13 pages.
International Search Report and Written Opinion in International Application No. PCT/US2009/044751, dated Feb. 17, 2010, 14 pages.
International Search Report and Written Opinion in International Application No. PCT/US2010/035616, dated Aug. 3, 2010, 13 pages.
International Search Report and Written Opinion in International Application No. PCT/U52005/026800, Mar. 28, 2007, 12 pages.
International Search Report and Written Opinion in International Application No. PCT/US2009/044714, dated Feb. 25, 2010, 16 pages.
International Search Report and Written Opinion of the International Searching Authority in PCT/US2008/056248, mailed Jun. 23, 2008, 11 pages.
Janssens et al., "Autologous bone marrow-derived stem-cell transfer in patients with ST-segment elevation myocardial infarction: double-blind, randomised controlled trial," Lancet, 2006, 367:113-121.
Kaltman et al., "Multipotent flk-1(+) cardiovascular progenitor cells give rise to the cardiomyocyte, endothelial, and vascular smooth muscle lineages," *Dev. Cell*, 2006, 11:723-732.
Kawai et al., "Efficient cardiomyogenic differentiation of embryonic stem cell by fibroblast growth factor 2 and bone morphogenetic protein 2," *Circ. J.*, 2004, 68:691702.
Kay et al., "Gene therapy," *Proc. Natl. Acad. Sci. USA*, 1997, 94:12744-12746.
Kehat et al., "Electromechanical integration of cardiomyocytes derived from human embryonic stem cells," *Nat. Biotechnol.*, 2004, 22:1282-1289.
Kirby, "Molecular embryogenesis of the heart," *Pediatr. Dev. Pathol.*, 2002, 5:516-543.
Kofidis et al., "Insulin-like growth factor promotes engraftment, differentiation, and functional improvement after transfer of embryonic stem cells for myocardial restoration," *Stem Cells*, 2004, 22:1239-1245.
Kolossov et al., "Engraftment of engineered ES cell-derived cardiomyocytes but not BM cells restores contractile function to the infarcted myocardium," J. Exp. Med., 2006, 203:2315-2327.
Kucia et al., "Bone marrow as a source of circulating CXCR4+ tissue-committed stem cells," *Biol. Cell*, 2005, 97:133-146.
Kucia et al., "Trafficking of normal stem cells and metastasis of cancer stem cells involve similar mechanisms: pivotal role of the SDF-I-CXCR4 axis," *Stem Cells*, 2005, 23:879-894.
Kulbe et al., "The chemokine network in cancer—much more than directing cell movement," *Int. J Dev. Biol.*, 2004, 48:489-496.
Kwon et al., "An essential role of N-terminal arginylation in cardiovascular development," *Science*, 2002, 297:96-99.
Laflamme and Murry, "Regenerating the heart," *Nat. Biotechnol.*, 2005, 23:845-856.
Lapidot and Kollet, "The essential roles of the chemokine SDF-1 and its receptor CXCR4 in human stem cell homing and repopulation of transplanted immune-deficient NOD/SCID and NOD/SCID/B2m(null) mice," *Leukemia*, 2002, 16:1992-2003.
Lapidot et al., "How do stem cells find their way home?" *Blood*, 2005, 106:1901-1910.
Lapidot, "Mechanism of human stem cell migration and repopulation of NOD/SCID and B2mnull NOD/SCID mice. The role of SDF-1/CXCR4 interactions," *Ann. N. Y. Acad. Sci.*, 2001, 938:83-95.
Lev et al. "Differentiation Pathways in Human Embryonic Stem Cell-Derived Cardiomyocytes," Ann. N.Y. Acad. Sci., 2005 1047: 50-65.
Levsky et al. (2002) Science, vol. 297, pp. 836-840.
Lough and Sugi, "Endoderm and heart development," *Dev. Dyn.*, 2000, 217:327-342.
Lough et al., "Combined BMP-2 and FGF-4, but neither factor alone, induces cardiogenesis in non-precardiac embryonic mesoderm," *Dev. Biol.*, 1996, 178:198-202.
Lunde et al., "Intracoronary injection of mononuclear bone marrow cells in acute myocardial infarction," *N. Engl. J. Med.*, 2006, 355:1199-1209.
Ma et al. "Intramyocardial delivery of human CD133+ cells in a SCID mouse cryoninjury model: Bone marrow vs. cord blood-derived cells," Cardiovascular Research, 2006, 71:158-169.
McGrath et al., "Embryonic expression and function of the chemokine SDF-1 and its receptor, CXCR4," *Dev. Biol.*, 1999, 213:442-456.
Menard et al., "Transplantation of cardiac-committed mouse embryonic stem cells to infarcted sheep myocardium: a preclinical study," *Lancet*, 2005, 366:1005-1012.
Meyer et al., "Intracoronary bone marrow cell transfer after myocardial infarction: eighteen months' follow-up data from the randomized, controlled BOOST (BOne marrOw transfer to enhance ST-elevation infarct regeneration) trial," Circulation, 2006, 113:1287-1294.

(56) References Cited

OTHER PUBLICATIONS

Molkentin et al., "Direct activation of a GATA6 cardiac enhancer by Nkx2.5: evidence for a reinforcing regulatory network of Nkx2.5 and GATA transcription factors in the developing heart," *Dev. Biol.*, 2000, 217:301-309.

Moretti et al., "Multipotent embryonic isl1+ progenitor cells lead to cardiac, smooth muscle, and endothelial cell diversification," *Cell*, 2006, 127:1151-1165.

Muller-Ehmsen et al., "Letters Regarding Article by Wojakowski et al., 'Mobilization of CD34/CXCR4+, CD34/CD117+, c-met+ Stem Cells, and Mononuclear Cells Expressing Early Cariac, Muscle and Endothelial Markers Into Periperal Blood Iin Patients with Acute Myocardial Infarction,'" Circulation, 2005, e307-e308, 3 pages.

Mummery et al. "Cardiomyocyte differentiation of mouse and human embryonic stem cells," *J. Anatomy*, 2002, 200(part 3):233-242.

Nagasawa et al., "Defects of B-celllymphopoiesis and bone-marrow myelopoiesis in mice lacking the CXC chemokine PBSF/SDF-1," *Nature*, 1996, 382:635-638.

Nakajima et al. "Transplantation of Flk1-postitive embryonic stem cells improves cardiac function after acute myocardial infarction in mice," *J. Heart and Lung Transplant.*, 2005, 24(2):S94 (Abstract only).

Nelson et al. "CXCR4 (+)/FLK-1 (+) biomarkers select a cardiopoietic lineage from embryonic stem cells," *Stem Cells*, 2008, 26(6):1464-1473.

Nelson et al., "Improved cardiac function in infarcted mice after treatment with pluripotent embryonic stem cells," *Anat. Rec.*, 2006, 288:1216-1224.

Office Action in Mexico Application No. MX/a/2010/012998, dated Oct. 22, 2012, 6 pages.

Perez-Terzic et al., "Stem cells transform into a cardiac phenotype with remodeling of the nuclear transport machinery," Nat. Clin. Pract. Cardiovasc. Med., 2007, 4(Suppl 1):S68-S76.

Pillarisetti and Gupta, "Cloning and relative expression analysis of rat stromal cell derived factor-1 (SDF-1)1: SDF-1 alpha mRNA is selectively induced in rat model of myocardial infarction," Inflammation, 2001, 25:293-300.

Rosenzweig, "Cardiac cell therapy—mixed results from mixed cells," N. Engl. J Med., 2006, 355:1274-1277.

Sanchez et al., "Contemplating the bright future of stem cell therapy for cardiovascular disease," Nat. Clin. Pract. Cardiovasc. Med., 2006, 3 Suppl.(1):S138-S151.

Schachinger et al., "Intracoronary bone marrow-derived progenitor cells in acute myocardial infarction," N. Engl. J. Med., 2006, 355:1210-1221.

Singla et al., "Transplantation of embryonic stem cells into the infarcted mouse heart: formation of multiple cell types," J. Mol. Cell. Cardiol., 2006, 40:195-200.

Smith et al., "Inhibition of pluripotential embryonic stem cell differentiation by purified polypeptides," Nature, 1988, 336:688-690.

Srivastava and Ivey, "Potential of stem-cell-based therapies for heart disease," *Nature*, 2006, 441:1097-1099.

Srivastava, "Making or breaking the heart: from lineage determination to morphogenesis," *Cell*, 2006, 126:1037-1048.

Sugi and Lough, "Activin-A and FGF-2 mimic the inductive effects of anterior endoderm on terminal cardiac myogenesis in vitro," *Dev. Biol.*, 1995, 168:567-574.

Tada et al., "Characterization of mesendoderm: a diverging point of the definitive endoderm and mesoderm in embryonic stem cell differentiation culture," *Development*, 2005, 132:4363-4374.

Taniuchi et al., "Dizygotic twin sisters with myelokathexis: mechanism of its neutropenia," Am. J. Hematol., 1999, 62:106-111.

Torella et al. "Cardiac stem cells regenerate the infarcted heart, restoring function and long-term survival in mice," Circulation, 2004, 110(17), Suppl III, 4 pages, (Abstract only; abstract on last page).

Tsai et al., "Functional Network Analysis of the Transcriptomes of Mesenchymal Stem Cells Derived from Amniotic Fluid, Amniotic Membrane, Cord Blood, and Bone Marrow," Stem Cells, 2007, 25:2511-2523.

Tsuji et al., "Xenografted Human Amniotic Membrane-Derived Mesechymal stem Cells are Immunologically Tolerated and Transdifferentiated Into Cardiomyocytes," Circulation Research, May 2010, 106:1613-1623 (Included Supplemental Materials).

Vandervelde et al., "Signaling factors in stem cell-mediated repair of infarcted myocardium," J. Mol. Cell Cardiol., 2005, 39:363-376.

Wobus et al., "Retinoic acid accelerates embryonic stem cell-derived cardiac differentiation and enhances development of ventricular cardiomyocytes," J. Mol. Cell Cardiol., 1997, 29:1525-1539.

Wojakowski et al., "Mobilization of CD34/CXCR4+, CD34/CD117+, c-met+ Stem Cells, and Mononuclear Cells Expressing Early Cariac, Muscle and Endothelial Markers Into Periperal Blood Iin Patients with Acute Myocardial Infarction," Circulation, Nov. 2004, 110:3213-3220.

Wu et al., "Developmental origin of a bipotential myocardial and smooth muscle cell precursor in the mammalian heart," Cell, 2006, 127:1137-1150.

Yamaguchi et al., "flk-1, an flt-related receptor tyrosine kinase is an early marker for endothelial cell precursors," *Development*, 1993, 118:489-498.

Yamashita et al., "Differentiation and diversification of vascular cells from embryonic stem cells," *Int. J. Hematol.*, 2004, 80(6808):92-96.

Yamashita et al., "Flk1-positive cells derived from embryonic stem cells servie as vascular progenitors," *Nature*, Nov. 2, 2000, 408:92-96.

Yamashita et al., "Perspective identification of cardiac progenitors by a novel single cell-based cardiomyocyte induction," *FASEB Journal*, 2005, 19:1534-1536.

Yasunaga et al., "Induction and monitoring of definitive and visceral endoderm differentiation of mouse ES cells," Nat. Biotechnol., 2005, 23:1542-1550.

Yuasa et al., "Transient inhibition of BMP signaling by Noggin induces cardiomyocyte differentiation of mouse embryonic stem cells," Nat. Biotechnol., 2005, 23:607-611.

Yusuf et al, "Expression of chemokine receptor CXCR4 during chick embryo development," *Anat. Embryol. (Berl)*, 2005, 210:35-41.

Zaffran and Frasch, "Early signals in cardiac development," *Circ. Res.*, Sep. 20, 2002, 91(6):457-469.

Zaffran et al., "Cardioblast-intrinsic Tinman activity controls proper diversification and differentiation of myocardial cells in *Drosophila*," *Development*, 2006, 133:4073-4083.

Zhu et al., "Evidence that FGF receptor signaling is necessary for endoderm-regulated development of precardiac mesoderm," *Mech. Ageing Dev.*, 1999, 108:77-85.

Zou et al., "Function of the chemokine receptor CXCR4 in haematopoiesis and in cerebellar development," Nature, 1998, 393:595-599.

European Office Action in European Application No. 05777528.0, dated Jan. 7, 2014, 5 pages.

European Office Action in European Application No. 05777528.0, dated Feb. 13, 2012, 4 pages.

European Office Action in European Application No. 05777528.0, dated Jul. 4, 2012, 3 pages.

European Office Action in European Application No. 10179541.7, dated Feb. 20, 2014, 6 pages.

Extended European Search Report in European Application No. 15171283.3 dated Oct. 19, 2015, 10 pages.

Summons to attend oral proceedings in European Application No. 09763198.0, dated Jun. 12, 2014, 5 pages.

United States Office Action in U.S. Appl. No. 11/572,874, mailed Jan. 12, 2009, 6 pages.

United States Office Action in U.S. Appl. No. 11/572,874, mailed Mar. 23, 2009, 11 pages.

United States Office Action in U.S. Appl. No. 11/572,874, mailed Apr. 29, 2010, 13 pages.

(56) References Cited

OTHER PUBLICATIONS

United States Office Action in U.S. Appl. No. 11/572,874, mailed Oct. 3, 2008, 9 pages.
United States Office Action in U.S. Appl. No. 11/572,874, mailed Nov. 16, 2009, 6 pages.
United States Office Action in U.S. Appl. No. 11/572,874, mailed Nov. 24, 2010, 12 pages.
United States Office Action in U.S. Appl. No. 12/530,165, mailed Feb. 17, 2012, 5 pages.
United States Office Action in U.S. Appl. No. 12/530,165, mailed May 25, 2012, 11 pages.
United States Office Action in U.S. Appl. No. 12/994,626, mailed Feb. 28, 2013, 18 pages.
United States Office Action in U.S. Appl. No. 12/994,626, mailed Jul. 24, 2012, 20 pages.
United States Office Action in U.S. Appl. No. 13/321,100, mailed Jul. 12, 2013, 14 pages.
United States Office Action in U.S. Appl. No. 13/433,095, mailed Feb. 20, 2014, 7 pages.
United States Office Action in U.S. Appl. No. 13/433,095, mailed Aug. 20, 2014, 6 pages.
United States Office Action in U.S. Appl. No. 13/433,095, mailed Aug. 7, 2013, 8 pages.
United States Office Action in U.S. Appl. No. 14/453,231, mailed Sep. 17, 2015, 7 pages.
United States Office Action in U.S. Appl. No. 13/231,100, mailed Jan. 2, 2014, 8 pages.
United States Office Action in U.S. Appl. No. 13/231,100, mailed Jun. 4, 2014, 6 pages.
United States Office Action in U.S. Appl. No. 13/231,100, mailed Jul. 17, 2015, 11 pages.
Nichols et al., "Formation of pluripotent stem cells in the mammalian embryo depends on the POU transcription factor OCt4," *Cell*, 1998, 95: 379-391.
Zingman et al., "Kir6.2 is required for adaptation to stress," *PNAS*, 2002, 99(20): 13278-13283.
United States Office Action in U.S. Appl. No. 14/453,231, mailed Feb. 25, 2016, 10 pages.
United States Office Action in U.S. Appl. No. 13/231,100, mailed Mar. 3, 2016, 6 pages.

\* cited by examiner

METHODS AND MATERIALS FOR PROVIDING CARDIAC CELLS

CLAIM OF PRIORITY

This application claims priority under 35 U.S.C. §119(e) to U.S. Patent Application Ser. No. 60/832,845, filed on Jul. 24, 2006, which is hereby incorporated by reference in its entirety.

BACKGROUND

1. Technical Field

This document relates to methods and materials involved in obtaining cardiac cells. For example, this document relates to methods and materials for providing mammalian heart tissue with cells that differentiate into cardiomyocytes.

2. Background Information

Cardiovascular disease is a leading cause of morbidity and mortality worldwide, despite advances in patient management (Towbin and Bowles, *Nature*, 415:227-233 (2002)). In contrast to tissues with high reparative capacity, heart tissue is vulnerable to irreparable damage (Anversa and Nadal-Ginard, *Nature*, 415:240-243 (2002)). Cell-based regenerative cardiovascular medicine is, therefore, being pursued in the clinical setting (Dimmeler et al., *J Clin Invest*, 115:572-583 (2005); Wollert and Drexler, *Circ Res*, 96:151-163 (2005); Caplice et al., *Nat Clin Pract Cardiovasc Med*, 2:37-43 (2005)).

SUMMARY

This document provides methods and materials relating to cardiac cells. For example, this document provides methods and materials that can be used to obtain cells having the ability to differentiate into cardiomyocytes. Such cells can be used to repair damaged heart tissue. For example, cells having the ability to differentiate into cardiomyocytes can be used to repair or regenerate heart tissue in patients with a cardiac condition (e.g., ischemic cardiomyopathy, myocardial infarction, or heart failure).

In general, one aspect of this document features a cell having the ability to differentiate into a cardiomyocyte, wherein the cell comprises an Nkx2.5 polypeptide and a MEF2C polypeptide associated with the nucleus of the cell. The DNA structure of the cell can be such that it is not modified through demethylation or histone deacetylation.

In another aspect, this document features a cell having the ability to differentiate into a cardiomyocyte, wherein the cell comprises an Nkx2.5 polypeptide, a MEF2C polypeptide, and a GATA4 polypeptide associated with the nucleus of the cell. The DNA structure of the cell can be such that it is not modified through demethylation or histone deacetylation.

In another aspect, this document features a cell having the ability to differentiate into a cardiomyocyte, wherein the cell is obtained by a method comprising contacting a stem cell with a composition under conditions wherein the stem cell differentiates into the cell, wherein the composition comprises at least five molecules selected from the group consisting of TGF-β, BMP, TNF-α, IGF-1, FGF-4, IL-6, LIF, VEGF-A, retinoic acid, and α-thrombin, provided that the composition comprises BMP, α-thrombin, or TNF-α when the composition comprises less than six of the molecules of the group. The cell can comprise a Nkx2.5 polypeptide, a MEF2C polypeptide, and a GATA4 polypeptide associated with the nucleus of the cell. The cell can maintain the ability to differentiate into a cardiomyocyte for 10 cell divisions if the cell is contacted with the composition for two days and the composition is removed from the cell after two days. The cell can maintain the ability to differentiate into a cardiomyocyte for 10 cell divisions if the cell is contacted with the composition for five days and the composition is removed from the cell after five days. The cell can form a sarcomere if the cell is contacted with the composition for 15 days. The cell can produce a calcium transient in response to an electrical current if the cell is contacted with the composition for 21 days. The cardiomyocyte can be a human cardiomyocyte. The stem cell can express CD105, CD166, CD29, and CD44 polypeptides and can lack expression of CD14, CD34, and CD45 polypeptides. The stem cell can be a mesenchymal stem cell. The stem cell can be a human mesenchymal stem cell. The stem cell can be obtained from human bone marrow. The at least one of the TGF-β, BMP, TNF-α, IGF-1, FGF-4, IL-6, LIF, VEGF-A, and α-thrombin can be a human polypeptide. Each of the TGF-β, BMP, TNF-α, IGF-1, FGF-4, IL-6, LIF, VEGF-A, and α-thrombin can be a human polypeptide. The composition can comprise between 2.5 ng per mL and 10 ng per mL of the TGF-β. The composition can comprise between 5 ng per mL and 20 ng per mL of the BMP. The composition can comprise between 5 ng per mL and 50 ng per mL of the TNF-α. The composition can comprise between $1 \times 10^{-6}$ μM and $2 \times 10^{-6}$ μM of the retinoic acid. The composition can comprise between 50 ng per mL and 100 ng per mL of IGF-1, between 10 ng per mL and 20 ng per mL of FGF-4, between 100 ng per mL and 200 ng per mL of IL-6, between 5 ng per mL and 200 ng per mL of VEGF-A, and 40 nM of α-thrombin. The composition can comprise BMP, α-thrombin, and TNF-α when the composition comprises less than six of the molecules of the group.

In another aspect, this document features a method for providing heart tissue with cardiomyocytes, wherein the method comprises administering, to the heart tissue, cells comprising Nkx2.5 polypeptides and MEF2C polypeptides associated with the nuclei of the cells. The cardiomyocytes can be human cardiomyocytes. The cells can be obtained by contacting stem cells with a composition under conditions wherein the stem cells differentiate into the cells, wherein the composition comprises at least five molecules selected from the group consisting of TGF-β, BMP, TNF-α, IGF-1, FGF-4, IL-6, LIF, VEGF-A, retinoic acid, and α-thrombin, provided that the composition comprises BMP, α-thrombin, or TNF-α when the composition comprises less than six of the molecules of the group. The stem cells can express CD105, CD166, CD29, and CD44 polypeptides, and can lack expression of CD14, CD34, and CD45 polypeptides. The stem cells can be mesenchymal stem cells. The stem cells can be human mesenchymal stem cells. The stem cells can be obtained from human bone marrow. The at least one of the TGF-β, BMP, TNF-α, IGF-1, FGF-4, IL-6, LIF, VEGF-A, and α-thrombin can be a human polypeptide. Each of the TGF-β, BMP, TNF-α, IGF-1, FGF-4, IL-6, LIF, VEGF-A, and α-thrombin can be a human polypeptide. The cell can maintain capacity for proliferation, capacity for nuclear translocation of cardiac transcription factors, capacity for sarcomeric organization, and capacity for calcium transient/contractile response to electrical stimulation provided by the heart tissue. The cell can have functional excitation contraction coupling.

In another aspect, this document features a method for providing heart tissue with cardiomyocytes, wherein the method comprises administering, to the heart tissue, cells comprising Nkx2.5 polypeptides, MEF2C polypeptides, and GATA4 polypeptides associated with the nuclei of the cells.

The cardiomyocytes can be human cardiomyocytes. The cells can be obtained by contacting stem cells with a composition under conditions wherein the stem cells differentiate into the cells, wherein the composition comprises at least five molecules selected from the group consisting of TGF-β, BMP, TNF-α, IGF-1, FGF-4, IL-6, LIF, VEGF-A, retinoic acid, and α-thrombin, provided that the composition comprises BMP, α-thrombin, or TNF-α when the composition comprises less than six of the molecules of the group. The stem cells can express CD105, CD166, CD29, and CD44 polypeptides, and can lack expression of CD14, CD34, and CD45 polypeptides. The stem cells can be mesenchymal stem cells. The stem cells can be human mesenchymal stem cells. The stem cells can be obtained from human bone marrow. The at least one of the TGF-β, BMP, TNF-α, IGF-1, FGF-4, IL-6, LIF, VEGF-A, and α-thrombin can be a human polypeptide. Each of the TGF-β, BMP, TNF-α, IGF-1, FGF-4, IL-6, LIF, VEGF-A, and α-thrombin can be a human polypeptide. The cell can maintain capacity for proliferation, capacity for nuclear translocation of cardiac transcription factors, capacity for sarcomeric organization, and capacity for calcium transient/contractile response to electrical stimulation provided by the heart tissue. The cell can have functional excitation contraction coupling.

In another aspect, this document features a composition comprising TGF-β, BMP, TNF-α, IGF-1, FGF-4, IL-6, LIF, VEGF-A, retinoic acid, and α-thrombin, wherein the composition comprises bovine serum albumin at $10^{-6}$ μM. The at least one of the TGF-β, BMP, TNF-α, IGF-1, FGF-4, IL-6, LIF, VEGF-A, and α-thrombin can be a human polypeptide. Each of the TGF-β, BMP, TNF-α, IGF-1, FGF-4, IL-6, LIF, VEGF-A, and α-thrombin can be a human polypeptide. The composition can comprise between 2.5 ng per mL and 10 ng per mL of the TGF-β. The composition can comprise between 5 ng per mL and 20 ng per mL of the BMP. The composition can comprise between 5 ng per mL and 50 ng per mL of the TNF-α. The composition can comprise between $1\times10^{-6}$ μM and $2\times10^{-6}$ μM of the retinoic acid. The composition can comprise between 50 ng per mL and 100 ng per mL of IGF-1, between 10 ng per mL and 20 ng per mL of FGF-4, between 100 ng per mL and 200 ng per mL of IL-6, between 5 ng per mL and 200 ng per mL of VEGF-A, and 40 nM of α-thrombin.

In another aspect, this document features a method for obtaining cells having the ability to differentiate into cardiomyocytes, wherein the method comprises contacting stem cells with a composition under conditions wherein the stem cells differentiate into the cells, wherein the composition comprises at least five molecules selected from the group consisting of TGF-β, BMP, TNF-α, IGF-1, FGF-4, IL-6, LIF, VEGF-A, retinoic acid, and α-thrombin, provided that the composition comprises BMP, α-thrombin, or TNF-α when the composition comprises less than six of the molecules of the group. The cells can comprise Nkx2.5 polypeptides associated with the nuclei of the cells and MEF2C polypeptides associated with the nuclei of the cells. The cells can comprise Nkx2.5 polypeptides associated with the nuclei of the cells, MEF2C polypeptides associated with the nuclei of the cells, and GATA4 polypeptides associated with the nuclei of the cells. The cells can maintain the ability to differentiate into cardiomyocytes for 10 cell divisions if the cells are contacted with the composition for two days and the composition is removed from the cells after two days. The cells can maintain the ability to differentiate into cardiomyocytes for 10 cell divisions if the cells are contacted with the composition for five days and the composition is removed from the cells after five days. The cells can form a sarcomere if the cells are contacted with the composition for 15 days. The cells can produce a calcium transient in response to an electrical current if the cells are contacted with the composition for 21 days. The cardiomyocytes can be human cardiomyocytes. The stem cells can express CD105, CD166, CD29, and CD44 polypeptides, and can lack expression of CD14, CD34, and CD45 polypeptides. The stem cells can be mesenchymal stem cells. The stem cells can be human mesenchymal stem cells. The stem cells can be obtained from human bone marrow. The at least one of the TGF-β, BMP, TNF-α, IGF-1, FGF-4, IL-6, LIF, VEGF-A, and α-thrombin can be a human polypeptide. Each of the TGF-β, BMP, TNF-α, IGF-1, FGF-4, IL-6, LIF, VEGF-A, and α-thrombin can be a human polypeptide. The composition can comprise between 2.5 ng per mL and 10 ng per mL of the TGF-β. The composition can comprise between 5 ng per mL and 20 ng per mL of the BMP. The composition can comprise between 5 ng per mL and 50 ng per mL of the TNF-α. The composition can comprise between $1\times10^{-6}$ μM and $2\times10^{-6}$ μM of the retinoic acid. The composition can comprise between 50 ng per mL and 100 ng per mL of IGF-1, between 10 ng per mL and 20 ng per mL of FGF-4, between 100 ng per mL and 200 ng per mL of IL-6, between 5 ng per mL and 200 ng per mL of VEGF-A, and 40 nM of α-thrombin. The composition can comprise BMP, α-thrombin, and TNF-α when the composition comprises less than six of the molecules of the group.

In another aspect, this document features a method for providing heart tissue with cardiomyocytes, wherein the method comprises administering, to the heart tissue, cells obtained by contacting stem cells with a composition, wherein the composition comprises at least five molecules selected from the group consisting of TGF-β, BMP, TNF-α, IGF-1, FGF-4, IL-6, LIF, VEGF-A, retinoic acid, and α-thrombin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
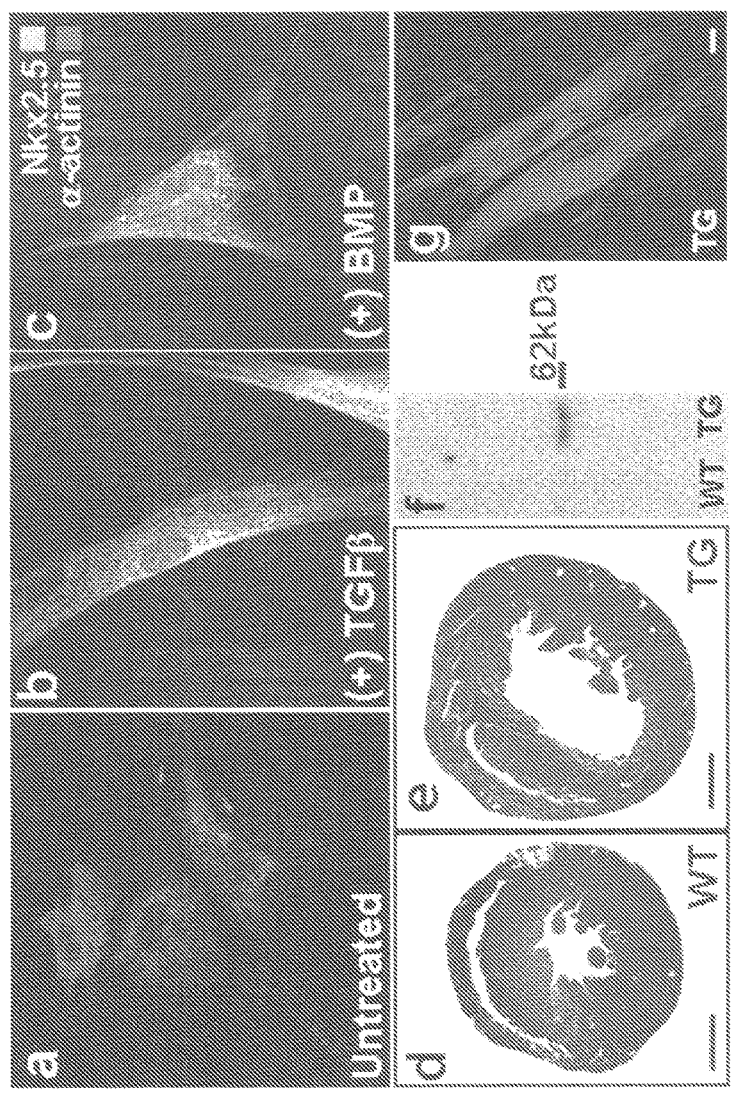
FIG. 1A is a photomicrograph of untreated human mesenchymal stem cells immunostained with Nkx2.5 and α-actinin antibodies.
FIG. 1B is a photomicrograph of TGF-β-treated human mesenchymal stem cells immunostained with Nkx2.5 and α-actinin antibodies.
FIG. 1C is a photomicrograph of BMP-treated human mesenchymal stem cells immunostained with Nkx2.5 and α-actinin antibodies.
FIG. 1D is a photomicrograph of a section of heart tissue from a wild-type mouse.
FIG. 1E is a photomicrograph of a section of heart tissue from a transgenic mouse overexpressing a TNF-α polypeptide under the control of a cardiac-specific promoter.
FIG. 1F is a photograph of a Western blot detecting TGF-β polypeptide expression in heart extracts from wild-type mice (WT) and transgenic mice overexpressing a TNF-α polypeptide under the control of a cardiac-specific promoter (TG).
FIG. 1G is a photomicrograph of fluorescent stem cells engrafted into the myocardium of a transgenic mouse overexpressing a TNF-α polypeptide under the control of a cardiac-specific promoter.

This document provides methods and materials related to cardiac cells and cells capable of differentiating into cardiac cells. For example, this document provides cells having the ability to differentiate into cardiac cells (e.g., cardiomyocytes), cardiac cells obtained from such cells, methods for making such cells, compositions for making such cells, and methods for using such cells to provide heart tissue with cardiac cells.

Cardiac cells can be any type of heart cells. For example, cardiac cells can be mammalian (e.g., human) heart cells. In some cases, cardiac cells can be cardiomyocytes. Cells having the ability to differentiate into cardiac cells can be any type of cells having the ability to differentiate into cardiac cells. For example, cells having the ability to differentiate into cardiac cells can be mammalian (e.g., human) cells having the ability to differentiate into cardiac cells. In some cases, cells having the ability to differentiate into cardiac cells can be referred to as cardiopoietic cells. The term cardiopoietic cell used herein refers to a cell having the ability to differentiate into a cardiomyocyte.

A cardiopoietic cell can be associated with a cardiac transcription factor. For example, a cardiopoietic cell can have a Nkx2.5, a MEF2C, or a GATA4 polypeptide, or any combination thereof associated with its nucleus. For example, a cardiopoietic cell can have a Nkx2.5, a MEF2C, and a GATA4 polypeptide associated with its nucleus. In some cases, the cardiopoietic cell can have a Nkx2.5, a MEF2C, or a GATA4 polypeptide, or any combination thereof associated with its cytoplasm. In some cases, a cardiopoietic cell can have one or more of a Nkx2.5, a MEF2C, or a GATA4 polypeptide associated with its nucleus and one or more of a Nkx2.5, a MEF2C, or a GATA4 polypeptide associated with its cytoplasm. For example, a cardiopoietic cell can have a Nkx2.5 polypeptide associated with its nucleus and a MEF2C polypeptide associated with its cytoplasm.

Any method can be used to obtain the cardiopoietic cells. For example, the cardiopoietic cells can be derived from stem cells such as mammalian (e.g., human) stem cells. In some cases, the cardiopoietic cells can be derived from embryonic stem cells. In one embodiment, the cardiopoietic cells can be derived from mesenchymal stem cells. Mesenchymal stem cells can be obtained from any source. For example, mesenchymal stem cells can be obtained from mammalian (e.g., human) tissue such as bone marrow and trabecular bone. Mesenchymal stem cells can be cultured in vitro. For example, mesenchymal stem cells can be expanded in number in vitro. The mesenchymal stem cell can express or not express a polypeptide marker on its cell surface. For example, the mesenchymal stem cell can express CD105, CD16, CD29, and CD44 on its cell surface and not express CD14, CD34, and CD45 on its cell surface.

Any method can be used to derive cardiopoietic cells from stem cells (e.g., mesenchymal stem cells). For example, cardiopoietic cells can be derived from mesenchymal stem cells by incubating the mesenchymal stem cells with a composition. The composition can be any composition containing one or more factors. The factors can be any type of factors such as polypeptides, steroids, hormones, and small molecules. Examples of such factors include, without limitation, TGF-β, BMP, TNF-α, IGF-1, FGF-4, IL-6, LIF, VEGF-A, retinoic acid, and α-thrombin. TGF-β can be any polypeptide having TGF-β activity, such as human TGF-β. For example, TGF-β can be recombinant TGF-β or synthetic TGF-β. In one embodiment, TGF-β can be TGF-β1. Any concentration of TGF-β can be used. For example, between 2.5 and 10 ng per mL of TGF-β can be used. BMP can be any polypeptide having BMP activity, such as human BMP. For example, BMP can be recombinant BMP or synthetic BMP. In one embodiment, BMP can be BMP-2. Any concentration of BMP can be used. For example, between 5 and 20 ng per mL of BMP can be used. TNF-α can be any polypeptide having TNF-α activity, such as human TNF-α. For example, TNF-α can be recombinant TNF-α or synthetic TNF-α. Any concentration of TNF-α can be used. For example, between 5 and 50 ng per mL of TNF-α can be used. IGF-1 can be any polypeptide having IGF-1 activity, such as human IGF-1. For example, IGF-1 can be recombinant IGF-1 or synthetic IGF-1. Any concentration of IGF-1 can be used. For example, between 50 ng per mL and 100 ng per mL of IGF-1 can be used. FGF-4 can be any polypeptide having FGF-4 activity, such as human FGF-4. For example, FGF-4 can be recombinant FGF-4 or synthetic FGF-4. Any concentration of FGF-4 can be used. For example, between 10 ng per mL and 20 ng per mL of FGF-4 can be used. IL-6 can be any polypeptide having IL-6 activity, such as human IL-6. For example, IL-6 can be recombinant IL-6 or synthetic IL-6. Any concentration of IL-6 can be used. For example, between 100 ng per mL and 200 ng per mL of IL-6 can be used. LIF can be any polypeptide having LIF activity, such as human LIF. For example, LIF can be recombinant LIF or synthetic LIF. Any concentration of LIF can be used. For example, between 2.5 ng per mL and 100 ng per mL of LIF can be used. VEGF-A can be any polypeptide having VEGF-A activity, such as human VEGF-A. For example, VEGF-A can be recombinant VEGF-A or synthetic VEGF-A. Any concentration of VEGF-A can be used. For example, between 5 ng per mL and 200 ng per mL of VEGF-A can be used. Retinoic acid can be any molecule having retinoic acid activity, such as synthetic retinoic acid, natural retinoic acid, a vitamin A metabolite, a natural derivative of vitamin A, or a synthetic derivative of vitamin A. Any concentration of retinoic acid can be used. For example, between $1 \times 10^{-6}$ and $2 \times 10^{-6}$ μM of retinoic acid can be used. α-Thrombin can be any polypeptide having α-thrombin activity, such as human α-thrombin. For example, α-thrombin can be recombinant α-thrombin or synthetic α-thrombin. Any concentration of α-thrombin can be used. For example, between 20 nM and 80 nM (e.g., 30 nM, 35 nM, 40 nM, 45 nM, or 50 nM) of α-thrombin can be used.

A composition provided herein can contain any combination of factors. For example, a composition provided herein can contain TGF-3, BMP, TNF-α, IGF-1, FGF-4, IL-6, LIF, VEGF-A, retinoic acid, and α-thrombin. In some cases, a composition provided herein can contain TGF-β, BMP, IGF-1, FGF-4, IL-6, LIF, retinoic acid, and α-thrombin. In some cases, a composition provided herein can contain TGF-β, BMP, IGF-1, FGF-4, IL-6, LIF, and VEGF-A. In some cases, a composition provided herein can contain BMP, IGF-1, FGF-4, IL-6, and LIF. In some cases, a composition provided herein can contain TGF-β, BMP, IGF-1, FGF-4, and α-thrombin. In some cases, a composition provided herein can contain TGF-β, BMP, TNF-α, IGF-1, and α-thrombin. In some cases, a composition provided herein can contain TGF-β, BMP, IGF-1, FGF-4, IL-6, LIF, VEGF-A, retinoic acid, and α-thrombin. In some cases, a composition provided herein can contain TGF-β, BMP, IGF-1, FGF-4, IL-6, LIF, VEGF-A, and α-thrombin.

A composition provided herein can be prepared using any method. For example, a composition provided herein can be prepared using commercially available factors. In some cases, a composition provided herein can be prepared using conditioned medium from cells such as cardiomyocyte cells or TNF-α-stimulated endodermal cells. In some cases, a composition provided herein can be prepared using conditioned medium supplemented with commercially available factors. In some cases, a composition provided herein can be prepared using factors isolated from conditioned medium. In some cases, the factors can be dissolved in medium such as cell culture medium that does or does not contain serum.

Any method can be used to incubate stem cells (e.g., mesenchymal stem cells) with a composition provided herein. For example, mesenchymal stem cells can be incubated with a composition provided herein for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days. In some cases, a composition provided herein and used to incubate the mesenchymal stem cells can be replaced everyday or every 2, 3, 4, 5, 6, 7, 8, 9, 10, 11, 12, 13, 14, 15, 16, 17, 18, 19, 20, 21, 22, 23, 24, 25, 30, 35, 40, 45, or 50 days. In some cases, mesenchymal stem cells can be incubated with a composition provided herein in the presence or absence of serum. In some cases, mesenchymal stem cells can be incubated with a composition provided herein in vitro or in vivo.

Once the mesenchymal stem cells have been incubated with a composition provided herein, differentiation of the mesenchymal stem cells can be monitored to determine whether or not the mesenchymal stem cells have differentiated into cardiac cells. For example, the cells can be tested for expression of a cardiac transcription factor such as Nkx2.5, MEF2C, GATA4, or any combination thereof. Any method can be used to test the cells for expression of a cardiac transcription factor including Western blotting, fluorescence-activated cell sorting (FACS), immunostaining, and laser confocal microscopy. In some cases, incubation of mesenchymal stem cells with a composition provided herein for two days can result in nuclear translocation of Nkx2.5 and up-regulation of cytosolic MEF2C expression. In some cases, incubation of mesenchymal stem cells with a composition provided herein for five days can result in nuclear translocation of both Nkx2.5 and MEF2C. Differentiation of the mesenchymal stem cells can also be monitored by testing the cells for sarcomere formation. Any method can be used to test the cells for sarcomere formation including immunostaining using α-actinin antibodies and laser confocal microscopy. In some cases, incubation of mesenchymal stem cells with a composition provided herein for 15 days can result in sarcomere formation. In addition, differentiation of the mesenchymal stem cells can be monitored by testing the cells for functional excitation-contraction coupling. Any method can be used to test the cells for functional excitation-contraction coupling. For example, excitation-contraction coupling can be recorded using laser confocal line scanning in Fluo 4-AM loaded cells to assess intracellular calcium dynamics following electrical stimulation at 1 Hz, and Zeiss LSM Image software can be used to analyze the data. In some cases, incubation of mesenchymal stem cells with a composition provided herein for 21 days can result in functional excitation-contraction coupling with rhythmic calcium transient activity.

Any method can be used to provide heart tissue with cardiac cells. For example, cardiac cells can be injected into the coronary artery, infused in the heart, administered systemically, or injected transendocardially. Any heart tissue can be provided with cardiac cells. For example, mammalian (e.g., human) heart tissue can be provided with cardiac cells. In some cases, heart tissue that has suffered from ischemic cardiomyopathy, myocardial infarction, or heart failure can be provided with cardiac cells. Any type of cardiac cells can be administered to heart tissue. For example, autologous or heterologous cardiac cells can be administered to heart tissue. In some cases, stem cells (e.g., mesenchymal stem cells) that were incubated with a composition provided herein can be administered to heart tissue. The stem cells can be incubated with a composition provided herein for any length of time before being administered to heart tissue. For example, the stem cells can be incubated with a composition provided herein for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days before being administered to heart tissue. In some cases, stem cells that were incubated with a composition provided herein can be administered to heart tissue together with a composition provided herein. The stem cells can be incubated with a composition provided herein for any length of time before being administered to heart tissue together with a composition provided herein. For example, the stem cells can be incubated with a composition provided herein for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days before being administered to heart tissue together with a composition provided herein. In some cases, stem cells can be administered to heart tissue together with a composition provided herein.

The invention will be further described in the following examples, which do not limit the scope of the invention described in the claims.

EXAMPLES

Example 1—Materials and Methods

Gene expression profiles of unprimed endodermal cells and endodermal cells primed with TNF-α were obtained by hybridizing labeled complementary RNA to the Mouse Genome 430 2.0 Array using standard protocols (Affymetrix, Santa Clara, Calif.). Data were acquired using a GeneChip Scanner 3000 (Affymetrix) and analyzed using GeneSpring software (Agilent Technologies, Palo Alto, Calif.). Data population sets were normalized to the unprimed or undifferentiated phenotype and quality filtered to eliminate background noise prior to hierarchical clustering. See, Behfar and Terzic, Nat Clin Pract Cardiovasc Med, 3 Suppl 1:S78-S82 (2006).

Mesenchymal stem cells were derived from human bone marrow withdrawn from the posterior iliac crest of the pelvic bone of 18- to 45-year-old healthy individuals (Cambrex, East Rutherford, N.J.). Based on flow cytometry analysis, the mesenchymal stem cells expressed CD105, CD166, CD29, and CD44, and did not express CD14, CD34, and CD45. The mesenchymal stem cells were cultured in DMEM (high glucose) containing 20% fetal bovine serum, penicillin, streptomycin, and L-glutamax (Invitrogen, Carlsbad, Calif.).

Human mesenchymal stem cells were plated at a density of 25,000 cells/25 cm$^2$ Falcon flask (BD Biosciences, Bedford, Mass.). The cells were treated with one or more recombinant cardiogenic agents (Sigma, Saint Louis, Mo.) for up to 21 days. Cardiogenic transformation was monitored by laser confocal microscopy (Zeiss, Oberkochen, Germany) following immunostaining using MEF2C (1:400; Cell Signaling Technology, Beverly, Mass.), Nkx2.5 (1:300; Santa Cruz Biotechnology, Santa Cruz, Calif.), and α-actinin (1:1,000; Sigma) antibodies.

Excitation-contraction coupling was monitored using laser confocal line scanning in Fluo 4-AM (Invitrogen) loaded cells to assess intracellular calcium dynamics following electrical stimulation at 1 Hz. Zeiss LSM Image software was used to analyze the data.

Example 2—Stimulation of Mesenchymal Stem Cells with TGF-β or BMP

Human bone marrow-derived mesenchymal stem cells (Pittenger and Martin, *Circ Res*, 95:9-20 (2004)) were stimulated with TGF-β or BMP (FIG. 1A-C). FIG. 1A shows light green and red fluorescent staining surrounding the nucleus of the cells indicating the presence of Nkx2.5 and MEF2C, respectively. FIGS. 1B and 1C display brighter green and red fluorescent staining for both Nkz2.5 and MEF2C; in both figures, the green fluorescent staining is more pronounced in the nucleus of the cells, while the cytoplasm displays a higher concentration of the red fluorescent stain. In contrast to unstimulated mesenchymnal stem cells that had low expression levels of cardiac transcription factors (Nkx2.5 and MEF2C; FIG. 1A), stimulation with TGF-β or BMP up-regulated cytosolic expression of cardiac transcription factors (FIGS. 1B and 1C). Stimulation with TGF-β or BMP did not, however, promote nuclear translocation of cardiac transcription factors (FIGS. 1B and 1C). The increase in cytosolic expression of Nkx2.5 and MEF2C in response to stimulation with TGF-β or BMP indicated that the human mesenchymal stem cells had a cardiogenic potential. Induction with individual cardiogenic factors was sub-optimal, however, in that it did not promote nuclear translocation of cardiac transcription factors, which is required for cardiogenesis.

Example 3—Identification of Cardiogenic Factors

Figure 2:
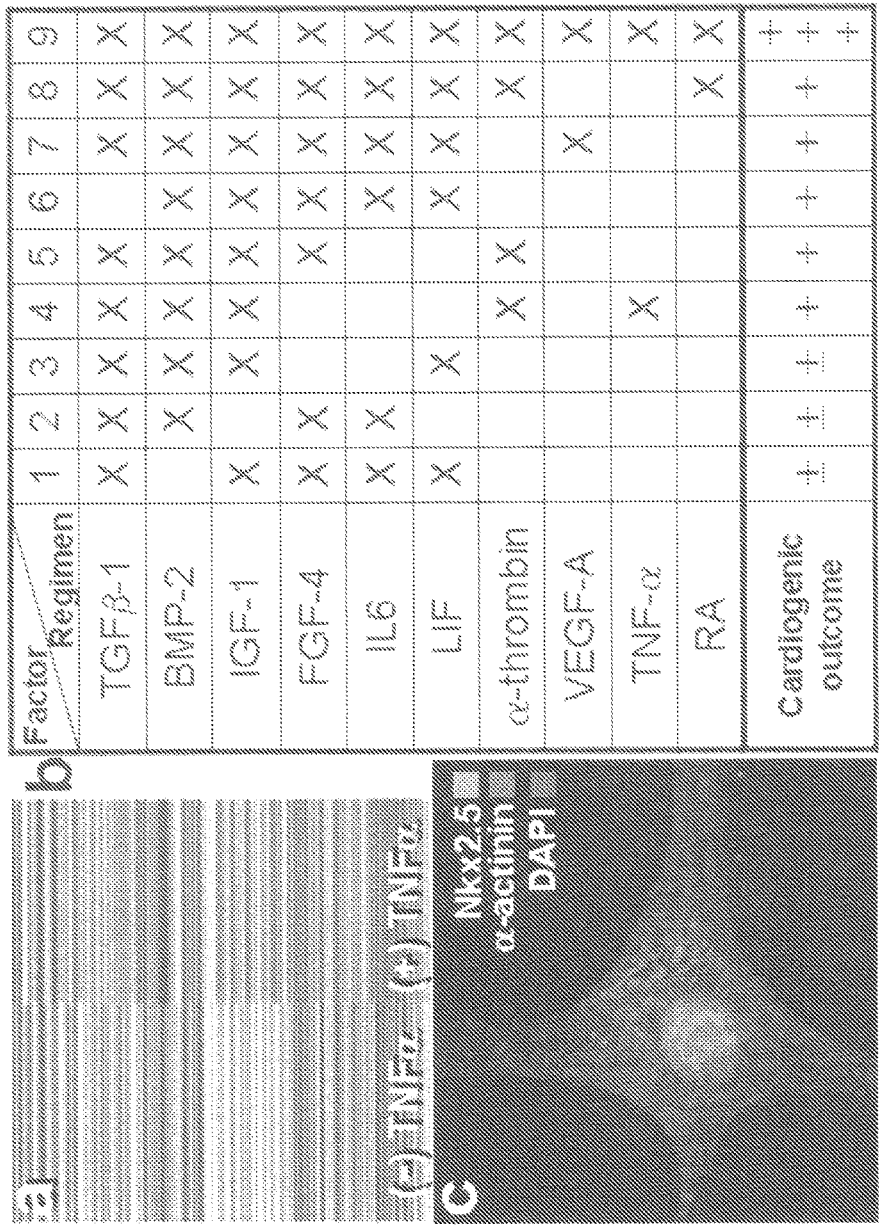
FIG. 2A is a genomic fingerprint of cardiogenic endodermal cells that were or that were not stimulated with a TNF-α polypeptide.
FIG. 2B is a table listing the cardiogenic outcome of human mesenchymal stem cells treated with the indicated combinations of cardiogenic factors.
FIG. 2C is a photomicrograph of a human mesenchymal stem cell treated with regimen 9 of FIG. 2B and stained with DAPI and antibodies to Nkx2.5 and α-actinin.

To advance the cardiac commitment of human bone marrow-derived mesenchymal stem cells, the factors necessary for cardiogenesis were identified. Cardiac-restricted transgenic overexpression of the cytokine TNF-α, which induces cardiomyopathy (Hodgson et al., *EMBO J*, 22:1732-1742 (2003); FIGS. 1D and 1E), was observed to stimulate TGF-β expression and result in cardiomyogenic transformation of transplanted stem cells (FIGS. 1F and 1G). FIG. 1G shows intense fluorescent blue staining indicative of overexpression of a TNF-α polypeptide. TGF-β alone does not induce cardiogenesis of human mesenchymal stem cells. Therefore, the effect of TNF-α was evaluated further in order to generate a comprehensive list of potential stem cell cardiogenic factors. A gene expression profile of cardiogenic endodermal cells (Mummery et al., *Circulation*, 107:2733-2740 (2003)) stimulated with TNF-α was generated using microarray technology. The mRNA levels of candidate cardiogenic factors were up-regulated (FIG. 2A). FIG. 2A displays an array of red and green strips with the green strips concentrated in the top two-thirds of the array, with an increase in red strips in the lower one-third. This list of candidate cardiogenic factors was refined by comparing it to the receptor profile of human mesenchymal stem cells (Pittenger and Martin, *Circ Res*, 95:9-20 (2004)) and selecting those factors for which the corresponding receptors are expressed on human mesenchymal stem cells. This list was further reduced to factors that induced up-regulation of cardiac transcription factors when applied to human mesenchymal stem cells. In addition to TGF-β, BMP, and TNF-α, these factors included insulin-like growth factor (IGF-1), fibroblast growth factor (FGF-4), interleukin 6 (IL-6), leukemia inhibitory factor (LIF), vascular endothelial growth factor (VEGF-A), retinoic acid (RA), and α-thrombin (FIG. 2B). A combination of at least five of the identified factors appeared necessary to induce a definitive cardiogenic response associated with nuclear translocation of cardiac transcription factors Nkx2.5 and MEF2C (FIGS. 2B and 2C). FIG. 2B displays an array similar to that seen in FIG. 2A, but the concentration of red and green striping is reversed. FIG. 2C illustrates a cell treated as in FIG. 2B, and shows a concentration of green (Nkx2.5) and blue (DAPI) staining in the nucleus with a large concentration of red (MEF2C) and a minor concentration of green staining in the surrounding area of the cell.

Figure 3:
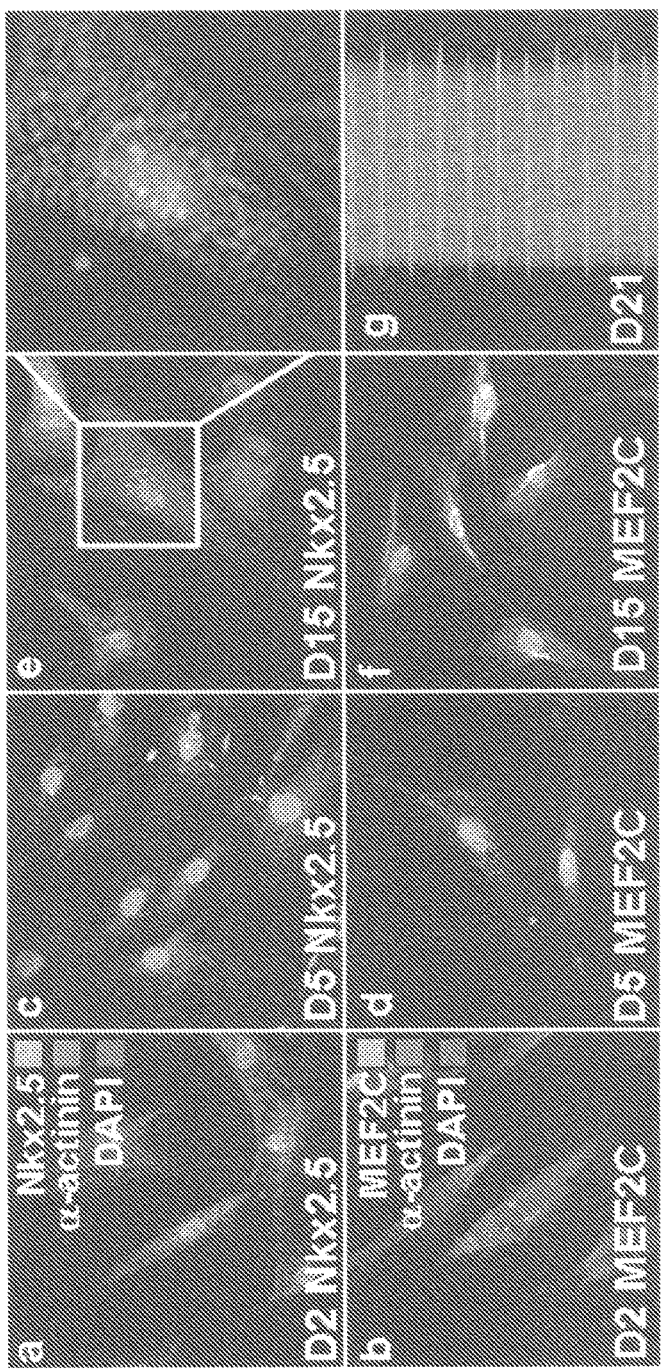
FIG. 3 contains a series of photomicrographs of human mesenchymal stem cells that were stimulated for 2 days (panels a and b), 5 days (panels c and d), 15 days (panels e and f), or 21 days (panel g) with regimen 9 of FIG. 2B and stained with antibodies to Nkx2.5 (panels a, c, and e) or MEF2C (panels b, d, and f) as well as antibodies to α-actinin (panels a-f). Panel g is a photomicrograph of a cell loaded with Fluo 4-AM to monitor rhythmic calcium transient activity upon pacing (1 Hz).

Example 4—Large-Scale Transformation of Mesenchymal Stem Cells Into Cardiopoietic Cells Regimen 9 (FIG. 2B) was used for large-scale transformation of human bone marrow-derived mesenchymal stem cells into cardiac progenitors, ensuring their cardiogenic homogeneity for clinical applications. Human bone marrow-derived mesenchymal stem cells treated with the identified cardiogenic cocktail (regimen 9, FIG. 2B) exhibited, by day two of stimulation, consistent nuclear translocation of the early cardiac transcription factor Nkx2.5 (FIG. 3A) and cytosolic up-regulation of MEF2C, a later factor in cardiac differentiation (FIG. 3B). FIGS. 3A and 3B show bright blue staining in the nucleus of the cells surrounded by a majority of green and a minority of red staining in the surrounding area. By day five, stimulation with the cardiogenic cocktail induced nuclear migration of both Nkx2.5 and MEF2C (FIGS. 3C and 3D). FIGS. 3C and 3D display cells having a mixture of bright green and blue staining in the nucleus with additional green staining surrounding the nucleus. This phenotype was consistent with that of a cardioprogenitor cardiopoietic cell, an intermediate cell type distinct from the human mesenchymal stem cell source and committed to cardiac transdifferentiation. Indeed, sarcomere formation was evident by day 15 of stimulation with the cardiogenic cocktail (FIGS. 3E and 3F). FIGS. 3E and 3F display bright green and blue staining in the nucleus with only red staining observed in the surrounding cytoplasm. By day 21, functional excitation-contraction coupling with rhythmic calcium transient activity was recorded (FIG. 3G), indicating derivation of functional cardiac progeny. FIG. 3G shows an array of bright green fluorescent striping accented with further green staining in the intervening areas.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing heart tissue with cardiopoietic cells capable of differentiating into cardiomyocytes, wherein said method comprises:
   (a) differentiating adult mesenchymal stem cells lacking expression of CD34 polypeptides into said cardiopoietic cells in vitro by contacting said adult mesenchymal stem cells with a composition under conditions wherein said adult mesenchymal stem cells differentiate into said cardiopoietic cells, wherein said composition comprises at least five molecules selected from the group consisting of TGF-β, BMP, TNF-α, IGF-1, FGF-4, IL-6, LIF, VEGF-A, retinoic acid, and α-thrombin, provided that said composition comprises BMP, α-thrombin, or TNF-α when said composition comprises less than six of said molecules of said group; and
   (b) administering said cardiopoietic cells to said heart tissue, wherein said cardiopoietic cells lack sarcomere formation as evidenced by an absence of a striated immunostaining pattern when stained with an anti-actinin antibody, and wherein said cardiopoietic cells have nuclear localization of Nkx2.5 polypeptides and MEF2C polypeptides.

2. The method of claim 1, wherein said cardiopoietic cells have nuclear localization of GATA4 polypeptides.

3. The method of claim 1, wherein said cardiopoietic cells are human cardiopoietic cells.

4. The method of claim 1, wherein said adult mesenchymal stem cells express CD105, CD166, CD29, and CD44 polypeptides and do not express CD14 and CD45 polypeptides.

5. The method of claim 1, wherein said adult mesenchymal stem cells are human mesenchymal stem cells.

6. The method of claim 1, wherein said adult mesenchymal stem cells are isolated from human bone marrow.

7. The method of claim 1, wherein at least one of said TGF-β, BMP, TNF-α, IGF-1, FGF-4, IL-6, LIF, VEGF-A, and α-thrombin is a human polypeptide.

8. The method of claim 1, wherein each of said TGF-β, BMP, TNF-α, IGF-1, FGF-4, IL-6, LIF, VEGF-A, and α-thrombin is a human polypeptide.

9. A method for obtaining cardiopoietic cells having the ability to differentiate into cardiomyocytes, wherein said method comprises contacting adult mesenchymal stem cells lacking expression of CD34 polypeptides with a composition under conditions wherein said adult mesenchymal stem cells differentiate into said cardiopoietic cells, wherein said composition comprises at least five molecules selected from the group consisting of TGF-β, BMP, TNF-α, IGF-1, FGF-4, IL-6, LIF, VEGF-A, retinoic acid, and α-thrombin, provided that said composition comprises BMP, α-thrombin, or TNF-α when said composition comprises less than six of said molecules of said group, wherein said cardiopoietic cells lack sarcomere formation as evidenced by an absence of a striated immunostaining pattern when stained with an anti-actinin antibody, and wherein said cardiopoietic cells have nuclear localization of Nkx2.5 polypeptides and MEF2C polypeptides.

10. The method of claim 9, wherein said cardiopoietic cells have nuclear localization of GATA4 polypeptides.

11. The method of claim 9, wherein said cardiopoietic cells maintain the ability to differentiate into cardiomyocytes for 10 cell divisions if said cardiopoietic cells are contacted with said composition for two, three, four, five, six, seven, eight, nine, ten, eleven, twelve, thirteen, or fourteen days and said composition is removed from said cardiopoietic cells after said two, three, four, five, six, seven, eight, nine, ten, eleven, twelve, thirteen, or fourteen days.

12. The method of claim 9, wherein said adult mesenchymal stem cells express CD105, CD166, CD29, and CD44 polypeptides and do not express CD14, CD34, and CD45 polypeptides.

13. The method of claim 9, wherein said adult mesenchymal stem cells are human mesenchymal stem cells.

14. The method of claim 9, wherein said composition comprises between 2.5 ng per mL and 10 ng per mL of said TGF-β.

15. The method of claim 9, wherein said composition comprises between $1 \times 10^{-6}$ μM and $2 \times 10^{-6}$ μM of said retinoic acid.

16. A method for providing heart tissue with cardiopoietic cells capable of differentiating into cardiomyocytes, wherein said method comprises administering said cardiopoietic cells to said heart tissue, wherein said cardiopoietic cells are obtained by contacting adult mesenchymal stem cells lacking expression of CD34 polypeptides with a composition, wherein said composition comprises at least five molecules selected from the group consisting of TGF-β, BMP, TNF-α, IGF-1, FGF-4, IL-6, LIF, VEGF-A, retinoic acid, and α-thrombin, wherein said cardiopoietic cells lack sarcomere formation as evidenced by an absence of a striated immunostaining pattern when stained with an anti-actinin antibody, and wherein said cardiopoietic cells have nuclear localization of Nkx2.5 polypeptides and MEF2C polypeptides.

17. The method of claim 1, wherein said mesenchymal stem cells are in contact with said composition for one, two, three, four, five, six, seven, eight, nine, ten, eleven, twelve, thirteen, or fourteen days.

* * * * *